United States Patent [19]

Liu

[11] Patent Number: 4,843,067
[45] Date of Patent: Jun. 27, 1989

[54] POLYSACCHARIDE CONTAINING PHARMACEUTICAL COMPOSITION FOR INCREASING THE IMMUNE FUNCTION

[76] Inventor: Yaguang Liu, 67-08 168th St., Flushing, N.Y. 11365

[21] Appl. No.: 932,404

[22] Filed: Nov. 19, 1986

[51] Int. Cl.$^4$ .................... A61K 35/78; A61K 31/715
[52] U.S. Cl. ...................... 514/54; 514/885; 536/123; 536/128; 424/195.1
[58] Field of Search .................. 514/54, 885; 536/123, 536/128; 424/195.1

[56] References Cited

U.S. PATENT DOCUMENTS

| | | | |
|---|---|---|---|
| 4,442,087 | 4/1984 | Kijima et al. | 424/195.1 |
| 4,528,188 | 7/1985 | Mitsuhashi et al. | 514/54 |
| 4,613,591 | 9/1986 | Aburada et al. | 514/34 |
| 4,684,628 | 8/1987 | Liu | 514/885 |
| 4,708,949 | 11/1987 | Liu | 514/27 |

FOREIGN PATENT DOCUMENTS

| | | | |
|---|---|---|---|
| 0030444 | 6/1981 | European Pat. Off. | 424/195.1 |
| 3042491 | 7/1982 | Fed. Rep. of Germany | 514/54 |
| 53-32107 | 3/1978 | Japan | 424/195.1 |
| 53-99313 | 8/1978 | Japan | 514/54 |
| 57-118519 | 7/1982 | Japan | 424/195.1 |
| 60-28933 | 2/1985 | Japan | 514/54 |

OTHER PUBLICATIONS

Kumazawa et al.; Immunology 47:75–83, (1982).
Ohno et al.; J. Pharm. Dyn. 6:903–912, (1983).
Kumazawa et al.; J. Pharm. Dyn. 8:417–424, (1985).
Kiyohara et al.; J. Pharmacobio. Dyn. 9:339–346, (1986).

*Primary Examiner*—Ronald W. Griffin
*Assistant Examiner*—Nancy S. Carson
*Attorney, Agent, or Firm*—Chenpatents

[57] ABSTRACT

A new pharmaceutical composition is composed of two plant extracts: Polysaccharides of Hunang QI and Polysaccharides of Dankuei. The pharmaceutical composition is highly effective in increasing immune function and is very safe. Methods of extracting polysaccharides of Huang QI from Astragalus membranaceus Bge or Astragalus gummifier Labillard, and polysaccharides of Dankuei from Angelica sinensis Diels, Angelic archangelica or Levisticum officinale Koch are disclosed.

7 Claims, No Drawings

POLYSACCHARIDE CONTAINING PHARMACEUTICAL COMPOSITION FOR INCREASING THE IMMUNE FUNCTION

BACKGROUND OF THE INVENTION

1. Field of the Invention

The present invention relates to pharmaceutical compounds useful for the increase of immune function and the prevention of infectious disease. The pharmaceutical composition is very safe.

2. Description of the Prior Art

U.S. Pat. No. 4,442,087 disclosed an interferon inducer isolated from tissue of a plant of the genus artemisia. U.S. Pat. No. 4,419,349 disclosed that the interferon inducer is believed to be a homogeneous polymer of protein and sugars containing phosphoric acid. U.S. Pat. No. 4,145,415 disclosed that three new active substances have therapeutic activity in mammals for improving or curing hepatic diseases, antitumor activity upon oral administration or antiinflammatory activity. U.S. Pat. No. 4,431,639 disclosed that an adjuvant is effective for stimulating the production of lymphocytes in the circulating blood of a mammal and the adjuvant is an extract from atractylis lyrata S. Meanwhile, The Journal of Tradition Chinese Medicine disclosed that the plant of Astragalus membranaceus has been used as a natural medicine for successfully treating common cold or acute upper respiratory tract infection in human. [The Journal of Tradition Chinese Medicine 21 (1): 71–76, 1980.]

SUMMARY OF THE INVENTION

It is an object of the present invention to provide safe and effective pharmaceutical composition for increasing immune function, hence preventing infectious disease.

In keeping with these objects and other objects which will become apparent hereinafter, the present invention resides, briefly stated, in a composition comprising a mixture of the following active ingredients:

1. The polysaccharides of Huang QI extracted from Astragalus Gummifier Labillard or Astragalus Membranaceus Bge or other Astragalus.

2. The polysaccharides of Dankuei is extracted from Levisticum officinale Koch, Angelica sinensis Diels or Angelica archangelica.

For the sake of convenience, composition comprising mixtures of the above extracts will hereinafter be referred to as "PCI" The initials shall have the following meanings. P: Pharmaceutical; C: Composition; I: Increasing Immune Function.

Although all of the above herbs have been individually utilized in traditional chinese herbal medicine for a variety of treatments, it has not been previously disclosed that the two active components in combination would produce a composition with the remarkable synergistic therapeutic effects of the compositions of the present invention.

The above herbs, Levisticum Officinale Koch and Astragalus Gummifier Labillard and Angelica archangelica are regarded and recognized by FDA of U.S. as safe.

DETAILED DESCRIPTION

According to the present invention, it has been found the pharmaceutical composition of these ingredients have a significant effects in increasing the immune function. It is expressly noted that the word composition has the meaning of compositions, since the composition herein used covers a range of active components. The immune system plays an important role in human body. The immune function normally protects human being from infections caused by viruses, bacteria, fungi, parasites and from developing cancer.

Obviously, it is very important that PCI must have two characteristics: a singificant increase of the immune function and its safeness without causing side effects safe.

PCI may be administered to patients in the form of capsules containing a powdered mixture of the active ingredients in appropriate proportions. Alternatively, tablets can be prepared to comprise the active ingredients and pharmaceutically acceptable binders, excipients, lubricants, sweeteners and coatings. A syrup or elixir of PCI may be prepared by dissolving PCI in alcohol or water together with suitable preservatives, sweeteners, dyes and flavoring agents. Ampules or vials of PCI for injection may likewise be prepared, with the PCI as prepared for oral administration and after being purified through further recrystallization and sterilization and the addition thereto of distilled water and other suitable solvents and additives known in the pharmaceutical art.

The PCI dosage units prepared according to the invention can be administered to patients with safety and increased immune function.

The compositions of the present invention comprise as their active components a mixture of two plants extracts: Polysaccharides of Hang QI and Polysaccharides of Dankuei.

The Polysaccharides of Huang QI is extracted from Astragalus Membranaceus Bge or Astragalus Gummifier Labillard or other species of Astragalus. Polysaccharides of Huang QI has the following structural formula:

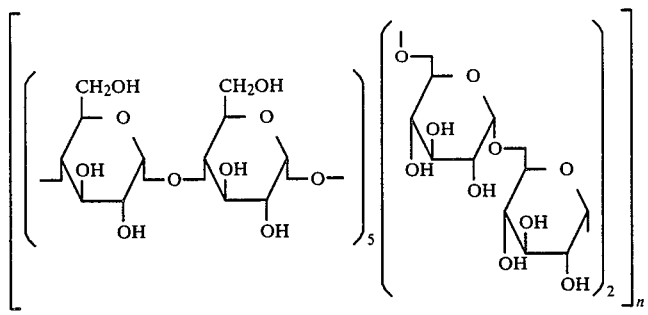

wherein n is from 100 to one million.

The following specific examples will provide detailed illustrations of methods of producing PCI according to the present invention and pharmaceutical dosage units containing PCI. Moreover, examples will be given by way of pharmacrutical testing performed with PCI to demonstrates its effectiveness in increasing immunofunction. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of Polysaccharides of Huang QI 2,000 ml of water was added to 1,000 g of dry powder of Astragalus Gummifier Labillard or Astragalus Membranaceus Bge or other species of Astragalus. The mixture was heated to boil and simmered for one and one-half hours after boiling. This water extraction was repeated once and the two extracts were combined and filtered. The filtrate was concentrated under reduced pressure to approximately 500 ml and 95% ethanol was added to the concentrate to yield a final alcohol concentration of 60%. The resulting solution was filtered to recover a precipitate which was dissolved in an appropriate amount of water, the resulting solution was filtered to remove residue and a filtrate was saved. The filtrate was concentrated under reduced pressure to 200 ml and 95% ethanol added to the concentrate to yield a final alcohol concentration of 80%. The solution was allowed to stand at 4 C. overnight. The supernatant was then discarded and the precipitate was washed three times with 95% ethanol and then twice with acetone and ether consecutively. The product was vacuum dried, and the resulting powder was astragalan.

EXAMPLE 2

Extraction of Polysaccharides of Dankuei from Levisticum officinale Koch, Angelica archangelica or Angelica sinensis Diels 1 kg of dried powder of Levisicum officinale Koch, Angelica archangelica or Angelica sinensis Diels was extracted with 5 liter of methanol in a water bath of 50° C. for 3 hours with stirring. The solution was filtered and the powder residue was saved. 5 liter of water were added to the residue. The mixture was heated to boil and simmered for 4–6 hours after boiling with stirring. This water extraction was repeated twice. The extracts were combined. 5 liter of 0.5N sodium hydroxide were added to the residue of water extraction and allowed to stand for 4–6 hours at room temperature. The sodium hydroxide extraction was repeated twice with fresh 0.5N sodium hydroxide. The extracts of water and sodium hydroxide were combined and centrifuged. The supernatant was collected and neutralized with 5N HCl. The neutral supernatant was dialysed against running $H_2O$ for two days. 5 volumes of 95% ethanol were added to the dialyzate. A precipitate was collected and dried by cold drying. The resulting powder was Polysaccharides of Dankuei.

EXAMPLE 3

Preparation of PCI

To prepare PCI, the two plants extracts prepared as described in the above examples 1–2 are thoroughly mixed to form a dry homogeneous composition. To achieve the therapeutic activities described herein, the proportions, by weight, of the individual components in the PCI are 50% to 95% of Polysaccharides of Huang QI and 5% to 40% of Polysaccharides of Dankuei.

One of the preferred proportions by weight percent of the individual components in the PCI are:

Polysaccharides of Huang QI: 83.4%,
Polysaccharides of Dankuei: 16.6%.

The most preferred compositions are: polysaccharides of Huang QI 55–90 wt.% and polysaccharides of Dankuei 10–35 wt.%. The components produced in accordance with the preceding examples, were thoroughly mixed and agitated until a homogeneous mixture of the two components was obtained.

EXAMPLE 4

PCI tablets 5 kg of PCI produced in accordance with the preceding example was combined with corn starch, dicalcium phosphate, potato starch, magnesium stearate and lactose. After further mixing, the aggregate was inserted into a tablet press and compressed into tablets suitable for oral adminstration. Each tablet contained 16.7 mg of Polysaccharides of Huang QI and 3.3 mg of Polysaccharides of Dankuei.

EXAMPLE 5

PCI solution 8.34 kg of Polysaccharides of Huang QI and 1.66 kg of Polysaccharides of Dankuei were thoroughly mixed in accordance with Example 3.

The resulting PCI powder was dissolved in a sufficient amount of sterile water and 4 volumes of 95% ethanol were added. The solution was allowed to stand for 24 hours and then filtered, with the ethanol being recovered under reduced pressure. 6 volumes of 95% ethanol were added to the residue. After standing for another 24 hours, the solution was filtered and ethanol recovered under reduced pressure. The residue was then distilled until there was no alcohol smell. Sufficient distilled water was added to dissolve the residue, and the solution was filtered to remove any undissolved material. Pharmaceutical glycerine was added to the solution. The solution was then fine filtered, and the volume was adjusted to the desired dosage by adding sufficient amount of distilled water. After additional fine filtering, the solution was sealed in 2 ml sterile ampules which were further sterilized and sealed. Each ampule contained 0.834 mg Polysaccharides of Huang QI and 0.166 mg of Polysaccharides of Dankuei.

The PCI elixir may be prepared by dissolving PCI in alcohol or water together with suitable preservatives, sweeteners, dyes and flavoring agents.

EXAMPLE 6

The effect of PCI on lymphoblastoid transformation by means of $^3$H-TdR liquid scintillation assay technique was investigated (1) Male mice weight 18–20 were used in the experiments. They were divided into three groups: normal, immunosuppressed and immunosuppressed+PCI. The PCI dosage of is 5.5 mg/kg was injected intraperitioneally to each of the mice in the immunosupressed+PCI group. The normal mice were injected with same volume of normal saline. These injections were repeated daily for 3–5 days. On the last day, both immunosuppressed and immunosuppressed+PCI groups were injected interapertioneally with one of the immunosuppressive agents including cortisone, cyclosporin A, prednisone, azathioprine, mercaptopurine, vincristine or chlorambucil. The experimental procedure for all the examples with mice is similar to the above procedures.

(2) Lymphoblastoid transformation test:
I. Reagents and conditions for cell culture
   a. Culture media—RPMI 1640, madium 199 minimal essential medium (Eagle).
   b. 37° C. to maintain the pH of the medium at 7.31.
   c. Serum—generally 15–20% fetal bovine serum was incorporated, for lymphocytes from mice, 5% was used.
   d. Gaseous phase 5% $CO_2$ in air.
   e. Cell concentration—generally 1–2×10/ml
   f. Stimulants—20 μl/ml for phytoagglutinin containing polysaccharide (PHA-M) or 10 μ/ml for polysaccharide-free purified phytoagglutinin (PHA-P).
II. Measured by liquid scintillation
   a. The conditions of cell culture are same as above. $^3$H-TdR is added after 48 hours of incubation at a final concentration of 2 μCi/ml and continue the incubation for 24 hours.
   b. Wash the cells twice with cold normal saline and lyse the erythrocytes by addition of distilled-water and equal volume of 3.6% NaCl was the added. Wash again the intact lymphocytes once with cold saline. Spin down the lymphocytes and add 2 ml of 10% trichloroacetic acid to precipitate the protein. Wash twice the normal saline. Add 2 ml of ethanol:ether (1:1) to wash once. 0.2 ml of formic acid is then added for digestion till the precipitate is dissolved.
   c. Add 4 ml of scintillation fluid to 0.1 ml of the final sample and count in a liquid scintillation counter.

(3) Results are listed in the following tables:

TABLE 1A

|  | Normal | Immuno-suppressed | Immuno-suppressed + PCI |
|---|---|---|---|
| CPM | 1340 ± 51 | 620 ± 58 | 1286 ± 54 |
| Number of sample | 10 | 10 | 10 |
| P | — |  | <0.01 |

* CPM: count per minutes

TABLE 1

|  | Normal | immuno-suppressed | Immuno-suppressed + PCI |
|---|---|---|---|
| Index of stimulation | 27.00 ± 3.20 | 13.12 ± 2.00 | 26.1 ± 1.20 |
| Number of sample | 12 | 12 | 12 |
| P | — |  | <0.1 |

EXAMPLE 7

The influence of PCI on formation of rosette in guinea pigs

I. Method
   1. Obtain venous blood in heparin (10 IU ml$^{-1}$) and perform a total and differential leucocyte count.
   2. Isolate lymphocyte fraction. Count vaiable lymphocytes calculate and record total yield. Adjust to $5 \times 10^6$ lymphocytes ml$^{-1}$.
   3. Wash sheep erythrocytes by centrifugation (400 g for 10 min. At room temperature) and adjust to a 2.5% v/v suspension in PBS.
   4. Mix 0.1 ml of the lymphocyte suspension with 0.1 ml of sheep erythrocytes and centrifuge at 225 g for 5 min. at room temperature.
   5. Incubate for 2 hours at 4° C.
   6. Add 50 μl of fetal bovine serum (FBS) and 50 μl of nigrosin solution.
   7. Resuspend cell mixture by gently tapping the tube and pipette a sample into a haemocytomer.
   8. Count 200 lymphocytes and determine the percentage of cells with 3 or more erythrocytes attached. (These are T lymphocytes)
   9. Calculate the absolute number of T lymphocytes ml$^{-1}$ of original blood.
II. Results are listed in the following table:

TABLE 2

|  | Normal (%) | Immuno-suppressed | Immuno-suppressed + PCI |
|---|---|---|---|
| Rate of formed rosette | 43.8 ± 2.0 | 20.7 ± 1.8 | 41.4 ± 3.6 |
| Number of sample | 12 | 12 | 12 |
| P | — |  | <0.01 |

EXAMPLE 8

The effect of PCI on phagocytosis of peritoneal macrophage of mice

Add 0.02 ml of 5% washed chick red blood cell suspension to 0.5 ml of the peritoneal exudate, shake gently to mix and incubate at 37° C. for 5 minutes. Dip two coverslips, close to each other, in the above mixture and incubate for 30 minutes for the migration of the macrophages along the cover slips, fix and stain with sharma stain. Examine microscopically for:

Phagocytic rate—number of macrophages with phagocytized chick red blood cells per 100 macrophages counted.

Results:

Results are illustrated in the following table:

TABLE 3A

|  | Normal | Immuno-suppressed | Immuno-suppressed + PCI |
|---|---|---|---|
| Phagocytic % ± SD % | 35.10 ± 2.01 | 19.8 ± 1.8 | 33.4 ± 2.7 |
| Number of samples | 10 | 10 | 10 |
| Probability | — |  | <0.1 |

(3) $^{63}Cr$ labeling method:

Method—Count the number of macrophages in the peritoneal exudate of mice and adjust to $1\times$ cell$^7$/ml with normal saline. Add 0.1 ml of the macrophage suspension i.e. $1\times 10^6$ cells to each well on the plastic plate for test. Label the chick red blood cell with $^{53}Cr$. Suspend the labelled chick red blood cell and adjust to $1.5\times 10^8$/ml, add 0.1 ml, thereof i.e. $1.5\times 10^7$, to each well. Incubate at 37° C. for 30 minutes. Wash thoroughly to remove the free chick red blood cells. Count each well in a Y-counter.

Results are listed bellow.

TABLE 3B

|  | Normal | Immuno-suppressed | Immuno-suppressed + PCI |
|---|---|---|---|
| CPM | 1089 ± 341 | 481 ± 44 | 908 ± 72 |
| Number of sample | 12 | 12 | 12 |
| P | — |  | <0.1 |

EXAMPLE 9

Influence of PCI on complement

Complement is a group of normal serum proteins. When the body is invaded by pathogenic microorganisms, complement acting together with specific antibodies exhibits its defensive function. It plays an important role in the anti-infectious immunity of the body. In addition, the complement system can also be activated by bacterial before the production of antibody by the body and achieves its bacteriocidal effect and inactivates the virus through the by-path.

1. Materials:
   a. Buffer stock:
   NaCl 85.00 g. Barbituric acid 5.75 g. Sodium barbital 3.75 g. Add 1500 ml of distilled water and heat to dissolve, add distilled water to 2000 ml.
   b. 0.1M EDAT—Na stock:
      EDTA—Na$_3$ 37.23 g, NaOH 4.00 g
      Add the EDTA—Na$_3$ to 500 ml of distilled water and the NaOH to 100 ml of distilled water. Add the later to the former and EDTA—Na$_3$ will dissolve instantly. Adjust PH to 7.5 with in NaOH and add distilled water to 1000 ml.
   c. 2% gelatin:
      Gelatin 2.0 g, distilled water 100 ml, heat to dissolve and store at 4° C.
   d. Gelatin Veronal Buffer (GVB)
      Buffer stock: 100 ml
      0.03M CaCl: 10 ml
      0.01M MgCl: 10 ml
      2% Gelatin: 100 ml
      Add distilled water to: 1000 ml
   e. Alsever solution:
      Glucose 20.5 g, NaCl 4.2 g, Sodium citrate 8.0 g dissolve in approximately 800 ml of distilled water and adjust PH to 6.1 with citric acid. Add distilled water to 1000 ml. Sterilize by autoclaving.
   f. 0.01M EDTA—GVB:
      Buffer stock 360 ml, 0.1M EDTA—Na$_3$ stock 200 ml, 2% Gelatin 100 ml, add distilled water to 2000 ml.
   g. SRBC:
      Mix fresh sterile sheep blood with equal volume of Alsever solution and store at 4° C. It can be used for several weeks.
   h. Hemolysin:
      (1) Preparation of SRBC stroma:
         Spin down the SRBC in liter of sheep blood—alsever solution and wash several times with normal saline. Add 10 liters of distileld water which contains 4 ml of glacial acetic acid. Suspend the RBC and let it sit in a 4° C. refrigerator overnight. Discard the supernatant and pack the settled stroma at 2,000 rpm. Suspend the stroma in 0.01M acetic acid solution. The acetic acid was then removed and the PH brought to neutral or slightly alkaline by wash the stroma 3 times each with 0.1M Na$_2$HPO$_4$ and normal saline. Pack the stroma by spinning at 7,500 rpm. The packed SRBC stroma was then suspended in 300–400 ml of normal saline. Heat to 100° C. for 1 hour. Determine the nitrogen content and adjust with sterile normal saline to 1 mg/ml. Add 0.01% merthiolate and store at 4° C.
      (2) Immunization of rabbits:
         Immunize the rabbits by 11 intravenous injections of the SRBC stroma in 2 weeks. Bleed the animals 4 days after the last injection. Separate the serum. Inactivate at 56° C. for 30 minutes and store at −20° C.
      (3) Titration for optimal concentration of heolysin:
         By using 50% hemolysin (C'H$_{50}$) as end-point, SRBC sensitized by various concentrations of hemolysin were titrated against various amounts of guniea pig complement. Optimal concentration of hemolysin was determined by OD$_{541}$ reading which gave C'H$_{50}$ and standard curve plotted.
   i. Serum samples for determination of complement content.
2. Methods:
   a. Preparation of SRBC suspension—wash SRBC for 5 times with GVB to free from platelets. Filter through gauze to remove cell aggregates.
   b. Preparation of sensitized SRBC—warm up 1 volume of hemolysin at the optimal concentration in a 37° C. water bath for 10 minutes and add equal volume of SRBC suspension at $1\times 10^9$ cells/ml with stirring. Let it sit in a water bath at 37° C. with shaking for 30 minutes. Then bring the temperature down in a ice-cool water bath shaking. Wash the cold SRBC once with 0.01M EDTA—GVB, twice with GVB and prepare sensitized SRBC suspension at $5\times 10^8$ cells/ml with GVB.
   c. Determination of C'H$_{50}$ unit and plotting of standard curves for the serum samples.

TABLE 4

| | Number of sample | Units (C'H$_{50}$)/ml |
|---|---|---|
| Normal | 18 | 509 ± 10 |
| Immuno-suppressed | 18 | 218 ± 9 |
| Immuno-suppressed + PCI | 18 | 327 ± 9 |
| P | | <0.01 |

EXAMPLE 10

The influence of PCI on particle clearance by the reticuloendothelial system

Method:
Spectrophotometer of colorimeter
(1) Warm the mouse at 37° C. for 15–20 minuts.
(2) Snip the end from the tail and collect one drop of blood onto a microscope slide. Lyse a 20 μl sample in 4.0 ml of acetic acid.
(3) Inject 0.1 ml of colloidal carbon into th tail vein. (Inject near to base of tail.)
(4) When the mouse's eyes have turn black (within 30 sec.) collect one drop of blood and lyse a 10 μl sample in 2 ml of acetic acid.
(5) Collect one drop of blood at the following times postinnoculation: 2. 5. 10. 15. 20. 30. 45. 60. 90. minutes and lyse a 10 l sample, before it clots, in 2 ml of acetic acid solution.
(6) Observe the colour change fo the mouse's eyes. Kill the mouse and examine.
(7) Using the original pre-injection blood sample as a standard read the density of all the lysed samples.

(by stuara A E. et al phagocytes in vitro in "handbook of Experimental immunology" Vol. 2 Cellular Immunology p. 31. 23. Third-ed weir DM Blackur Oxford. 1978. London)

TABLE 5

| | Normal | Immuno-suppressed | Immuno-suppressed + PCI |
|---|---|---|---|
| Particle clearance | 4.53 ± 0.03 | 2.08 ± 0.2 | 4.04 ± 0.1 |
| Number of sample | 18 | 18 | 18 |
| P | — | | <0.1 |

EXAMPLE 11

Effects of PCI on immune function of human blood lymphocytes 20 old volunteers (60–70 years of age) and 10 healthy young persons participated in the experiment.

2 ml of venous blood, heparinized was obtained from each of the participants. The study of the effects of PCI was carried out by using Eagle's Minimal Essential Medium (MEM). MEM was supplemented with 0.125 ml of heat-inactivated fetal calf serum, 100 units of Penicillin and 0.1 mg of streptomycin per ml of medium. Culture medium was divided into treated (PCI) and control group. PCI was added to the culture medium of PCI group ( a final ethanol concentration is 150 μg/ml on the 72 hours of culture. The culture medium of control group was mixed with same volume as that of PCI of normal saline on the 72 hours of culture. The $^3$H-thymidine ($^3$H-TdR) was added into all the cultures (2 μci/ml) for last 12 hours of culture. The cells were harvested on 0.45 μm millipore filters, washed with phosphate buffer (ph 7.4) and bleached with $H_2O_2$. The filters were then dried and the incorporation of $^3$H-TdR into lymphocytes cell was measured by scintillation counter.

TABLE 6

| | Young (n = 10) | | Old (n = 20) | |
|---|---|---|---|---|
| | Control | PCI | Control | PCI |
| CPM/10 cells | 8527 ± 2009 | 36286 ± 2119 | 22498 ± 1895 | 33948 ± 2018 |
| T/C | | 101.0% | | 138.5% |
| P | | <0.5 | | <0.01 |

According to Table 6, PCI was found to increase lymphoblastoid transformation of the old persons. However, PCI was found to add nothing to the young persons. In other words, PCI can increase human immune function in immunosuppressive state.

EXAMPLE 12

Safeness of PCI

1. L.D$_{50}$: 6381 mg/kg injection in abodominal cavity in mice.
2. Each dose for an adult is 20 mg. Assuming 50 kg to be the average weight of an adult. The dosage is 0.4 mg/kg, therefore it is very safe.

According to Table 1–5, PCI was found to obviously increase the immune function.

The preparation of PCI is simple and can be accomplished by the extraction methods set forth above or any conventional methods for extracting the active ingredients from the plant tissues. The novelty of the present invention resides in the mixture of the active ingredients in the specified proportions to produce PCI and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, tablets, capsules, syrups, elixirs, and solutions for parenteral injection with specified ranges of PCI concentration.

The present invention provides novel methods for increasing immunofunction with easily produced, safe pharmaceutical compositions.

It has been shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims:

1. A composition pharmaceutically effective for increasing the immune function in humans comprising:
polysaccharides of Huang QI 50–95% by weight and
polysaccharides of Dankuei 5–40% by weight.
2. A composition according to claim 1 wherein said polysaccharides of Huang QI are extracted from a plant selected from the group consisting of Astragalus gummifier Labillard, and Asragalus membranaceus Bge and said polysaccharides of Dankuei are extracted from a plant selected from the group consisting of Levisticum officinale Koch, Angelica sinensis Diels and Angelica archangelica.

3. A process for producing polysaccharides of Huang QI from Astragalus gummifier Labillard or Astragalus membranaceus Bge comprising:
(a) extracting a powder of one of the above mentioned plant with water by boiling first and then simmering for at least an hour;
(b) filtering the extract from the powder residue;
(c) concentrating the extract under reduced pressure;
(d) adding 95% ethanol to the concentrate of c, to produce a 60% ethanol solution to form a precipitate;
(e) separating the precipitate from the ethanol solution;
(f) dissolving the precipitate in water and filtering to remove any undissolved solids;
(g) concentrating the filtrate of (f) under reduced pressure;
(h) adding 95% ethanol to the concentrated filtrate to yield an 80% ethanol solution;
(i) cooling the 80% ethanol solution to form a precipitate;
(j) separating the precipitate and drying same under vacuum to yield a final powder product.

4. The process of claim 3 further comprising the steps of purification by:
(k) washing said product with 95% ethanol three times;
(l) washing the product of (k), consecutively with acetone and ether twice and
(m) vacuum drying the product of (l).

5. A process for producing polysaccharides of Dankuei from Levistiocum officinal Koch, Angelica archangelica or Angelica sinensis Diels comprising:
(a) extracting a powder of Levisticum officinale Koch, Angelica archangelica or Angelica sinensis Diels with methanol at 50° C. for about 3 hours;
(b) separating the extract from the powder residue;
(c) extracting the resulting residue of (b) with water by boiling and simmering;
(d) separating the water extracts from the residue of (c);
(e) extracting the residue of (d) with 0.5N sodium hydroxide and separating the resulting extract from the residue;
(f) combining the water extracts of (d) and sodium hydroxide extracts of (e) and centrifuging same;
(g) recovering and neutralizing the resulting supernatant liquid;
(h) dialyzing the neutralized supernatant liquid against running water to isolate the polysaccharides;
(i) precipitating the product by adding 95% ethanol to the dialyzate, and
(j) recovering and drying the product.

6. A method for treatment of immunosuppression in humans comprising administering to said humans suffering therefrom a therapeutically effective dose of a composition comprising polysaccharides of Huang QI 50-95 wt.% and polysaccharides of Dankuei 5-40 wt.%.

7. The method of claim 6 wherein the effective dosage is about 20 mg per 50 kg of body weight.

* * * * *